United States Patent [19]

Lizardi et al.

[11] Patent Number: 5,423,860
[45] Date of Patent: Jun. 13, 1995

[54] PROTECTIVE CARRIER FOR SUTURE ANCHOR

[75] Inventors: Jose E. Lizardi, Medfield; John D. Unger, Wrentham, both of Mass.

[73] Assignee: American Cyanamid Company, Wayne, N.J.

[21] Appl. No.: 68,938

[22] Filed: May 28, 1993

[51] Int. Cl.⁶ ............................................. A61B 17/00
[52] U.S. Cl. ...................... 606/232; 606/72; 606/75
[58] Field of Search .............. 606/72, 75, 78, 139, 606/144, 232, 213, 219; 604/57, 59, 60

[56] References Cited

U.S. PATENT DOCUMENTS

| | | |
|---|---|---|
| 2,765,828 | 10/1956 | Leniz . |
| 3,316,949 | 5/1967 | Canfield . |
| 3,620,216 | 11/1971 | Szymanski ............... 604/60 |
| 4,235,238 | 11/1980 | Ogiu et al. . |
| 4,631,985 | 12/1986 | Roberts . |
| 4,632,100 | 12/1986 | Somers et al. . |
| 4,704,929 | 11/1987 | Osada . |
| 4,738,255 | 4/1988 | Goble et al. ............. 606/232 |
| 4,741,330 | 5/1988 | Hayhurst . |
| 4,776,328 | 10/1988 | Frey et al. ............... 606/72 |
| 4,968,315 | 11/1990 | Gatturna ................. 606/232 |
| 5,037,422 | 8/1991 | Hayhurst et al. . |
| 5,059,206 | 10/1991 | Winters .................. 606/213 |
| 5,100,417 | 3/1992 | Cerier et al. . |
| 5,141,520 | 8/1992 | Goble et al. . |
| 5,192,303 | 3/1993 | Gatturna et al. ......... 606/232 |
| 5,207,679 | 5/1993 | Li . |
| 5,224,946 | 7/1993 | Hayhurst et al. ........ 606/232 |
| 5,258,016 | 11/1993 | DiPoto et al. ........... 606/72 |
| 5,268,001 | 12/1993 | Nicholson et al. ....... 606/72 |
| 5,324,308 | 6/1994 | Pierce .................... 606/232 |
| 5,336,240 | 8/1994 | Metzler et al. .......... 606/232 |

Primary Examiner—Ralph A. Lewis
Attorney, Agent, or Firm—D. E. Denninger

[57] ABSTRACT

A protective carrier having a sleeve body with a distal end, a proximal end, and a passageway extending longitudinally between them. One or more elements are disposed in the passageway proximate to the distal end for interlocking with a suture anchor to capture the suture anchor at least partially within the sleeve body. The carrier further includes one or more elements for aligning the sleeve body with a distal portion of a suture anchor driver to inhibit rotation of the sleeve body relative to the driver during and after insertion of the distal driver portion through the passageway.

9 Claims, 4 Drawing Sheets

5,423,860

PROTECTIVE CARRIER FOR SUTURE ANCHOR

FIELD OF INVENTION

This invention relates to a detachable, disposable device which carries and protects a suture anchor during handling and surgical implantation of the suture anchor, and more particularly to such a device which facilitates loading of the suture anchor onto a driver and delivery into a patient.

BACKGROUND OF THE INVENTION

Ligaments, tendons, and other soft tissue are routinely secured in place by surgical suture attached to a suture anchor implanted in a patient. Two types of suture anchors are disclosed in U.S. Pat. Nos. 5,037,422 and 5,100,417, incorporated herein by reference. These suture anchors are currently sold as TAG TM Rod-Style and Wedge-Style anchors by Acufex Microsurgical, Inc., of Mansfield, Mass., a subsidiary of American Cyanamid Company, Wayne, N.J.

Each suture anchor is implanted using an appropriate driver. The Rod-Style anchor snap-fits directly onto a distal post of a driver. The Wedge-Style anchor has an inner cavity which receives a rounded distal tip of a driver.

Another type of suture anchor, disclosed in U.S. Pat. No. 5,207,679, has a plurality of elastically deformable barbs. A driver for this anchor has a central bore surrounded by a plurality of longitudinally-extending stainless steel projections. During use, the anchor is inserted into the bore, and the projections frictionally engage the outer surface of the anchor. A similar driver is sold as the Mini GII Inserter, Catalog No. 212069, by Mitek Surgical Products, Inc., Norwood, Mass. The Mini GII Inserter has a cylindrical plastic tip which is rotatably but nonremovably attached to a metal shaft of a central bore surrounded by four longitudinal finger-like projections which frictionally engage the anchor.

A number of suture anchors are supplied to surgeons without suture secured thereto to enable each surgeon to select an appropriate absorbable or non-absorbable suture for a particular surgical application. An opening in the anchor must be aligned with the selected suture, and the suture then is passed through the opening. Manipulation of the anchor relative to the suture becomes increasingly difficult for smaller-sized anchors.

Further, contact with the anchor itself should be minimized after sterilization to preserve sterility. Attempting to thread a suture through the anchor and to load the anchor onto a driver may presently result in dropping the anchor or otherwise provide opportunities for inadvertent contamination of the anchor. Mishandling of a suture anchor could also result in breakage of the anchor.

SUMMARY OF THE INVENTION

Therefore, it is an object of the present invention to provide a protective carrier for a suture anchor which facilitates manipulation of the suture anchor.

It is a further object of this invention to provide such a protective carrier which minimizes dropping and inadvertently contaminating the suture anchor.

A still further object of this invention is to provide such a protective carrier which reduces contact between a user and the suture anchor.

Another object of this invention is to provide such a protective carrier which minimizes damage to the suture anchor prior to and during implantation.

It is a further object of this invention to provide such a protective carrier which is inexpensive, easy to manufacture, and disposable.

Yet another object of this invention is to provide a combination of a protective carrier and suture anchor within a package that facilitates loading of the protective carrier onto a driver.

This invention features a protective carrier having a sleeve body with a distal end, a proximal end, and a passageway extending longitudinally therebetween. One or more elements are disposed in the passageway proximate to the distal end for interlocking with a suture anchor to capture the suture anchor at least partially within the sleeve body. The carrier further includes one or more elements for aligning the sleeve body with a distal portion of a suture anchor driver to inhibit rotation of the sleeve body relative to the driver during and after insertion of the distal driver portion through the passageway.

In one embodiment, the element for interlocking includes one or more flanges projecting into the passageway, such as two arcuate flanges extending substantially parallel to the distal end of the sleeve body. Alternatively, the interlocking element is at least one recess defined within the sleeve body for engaging a matching projection of the suture anchor. The element for aligning includes one or more ribs projecting into the passageway, each rib being removably insertable into a corresponding groove in the distal driver portion. The sleeve body may further include one or more slots in the distal end of the sleeve body for accommodating a portion of a suture carried by the suture anchor.

This invention also features a combination of a suture anchor, a protective carrier as described above, and a package for carrying the protective carrier with a captured suture anchor. The protective carrier may further include one or more flat faces extending longitudinally along a portion of the outer surface of the sleeve body, and the package defines a recess having a wall engageable with the flat face to inhibit rotation of the protective carrier relative to the package. Preferably, the recess is inclined to expose the proximal end of the protective carrier to enable insertion of the distal driver portion into the passageway.

This invention further features a combination of a suture anchor, a driver, and a protective carrier as described above. This combination may further include a suture carried by a suture anchor.

BRIEF DESCRIPTION OF THE DRAWINGS

Other objects, features and advantages will occur from the following description of a preferred embodiment and the accompanying drawings, in which.

DETAILED DESCRIPTION OF THE PREFERRED EMBODIMENT

Figure 1:
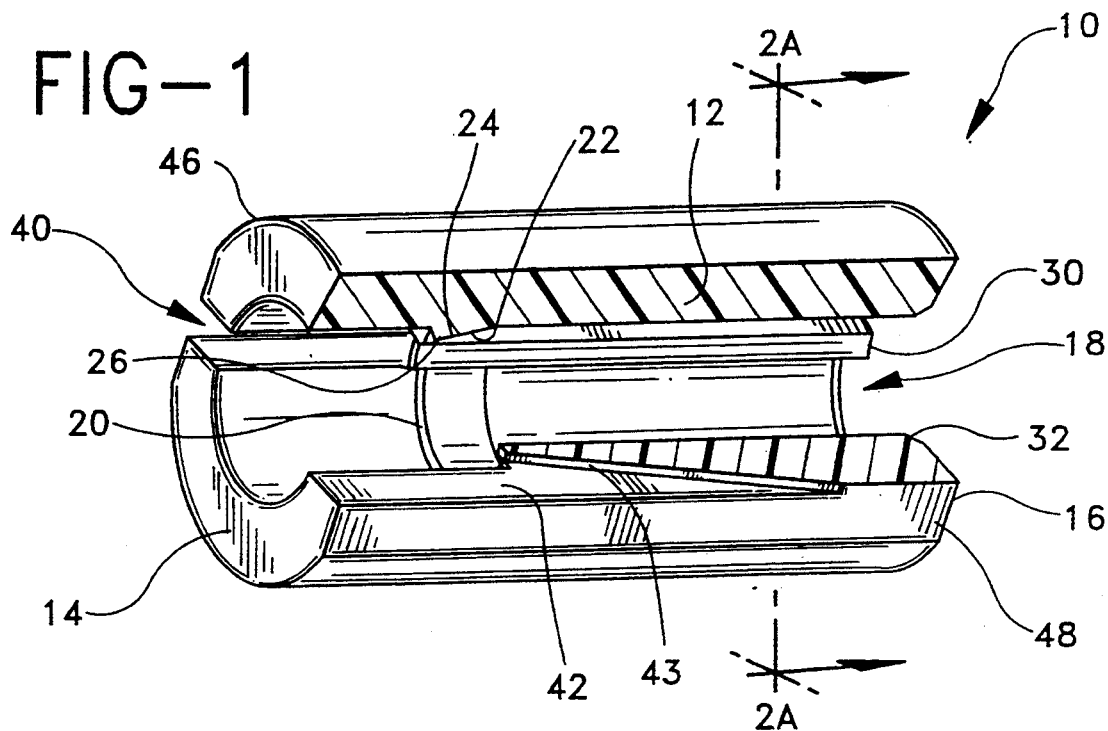
FIG. 1 is an axonometric, partial-cutaway view of a protective carrier according to this invention.
Figure 2A:
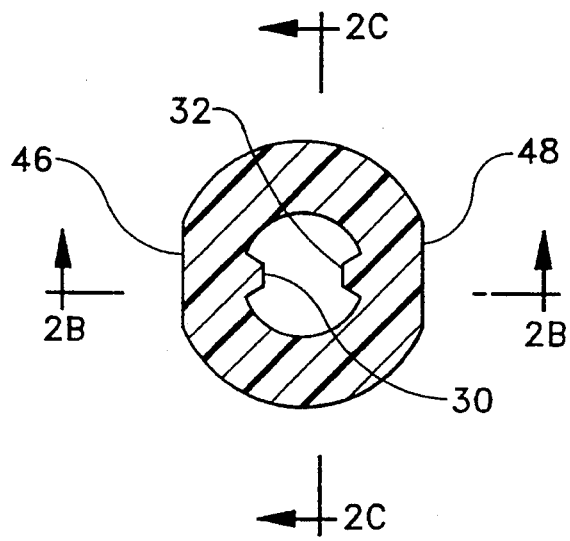
FIG. 2A is lateral cross-sectional view through the carrier of FIG. 1 along lines 2A—2A.
Figure 2B:
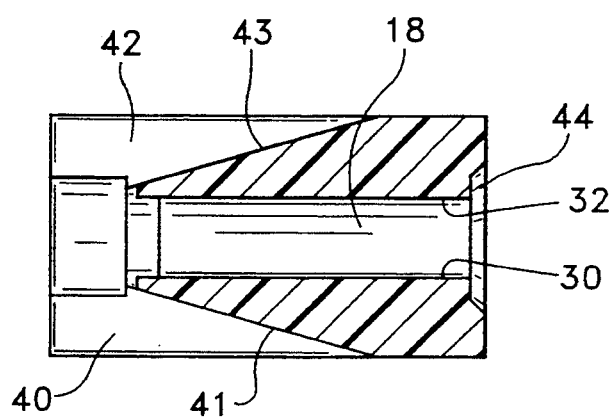
FIGS. 2B and 2C are longitudinal cross-sectional views rotated ninety degrees from each other along lines 2B—2B and 2C—2C in FIG. 2A.
Figure 2C:
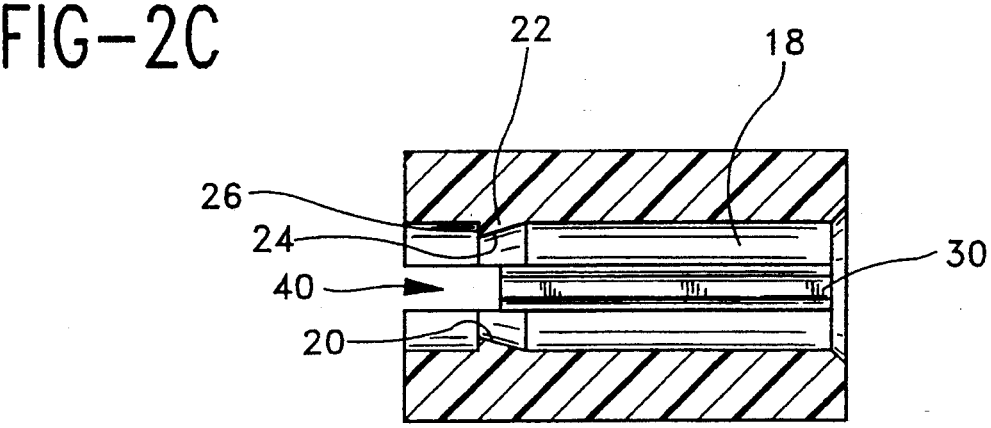

This invention may be accomplished by a protective carrier 10, FIGS. 1-2C, having a sleeve body 12 with a distal end 14, a proximal end 16, and a passageway 18 extending longitudinally therethrough. The sleeve body 10 is cylindrical in this construction. A pair of arcuate flanges 20, 22 extend substantially parallel to the distal end 14. Each flange has a shallow proximal inclined face 24 and a steeply inclined distal face 26 as shown for flange 22. These flanges project radially inwardly to interlock with a suture anchor to capture it as described in more detail below.

The protective carrier 10 further includes a pair of ribs 30, 32, for aligning the sleeve body 12 with a distal portion of a suture anchor driver to inhibit rotation of the sleeve body 12 relative to the driver during and after insertion of the distal driver portion through a passageway 18. Alternatively, the alignment mechanism is a non-circular cross-section or other offset-type feature which matches the shape of a corresponding driver to inhibit relative rotation.

A pair of inclined slots 40, 42, FIGS. 1 and 2B, accept a suture carried by a suture anchor as shown in U.S. Pat. Nos. 5,037,422 and 5,100,417, incorporated herein by reference. The slots extend radially completely between passageway 18 and the outer surface of the sleeve body 12 at the distal end, as shown in FIGS. 1 and 2C for slot 40; the slots 40, 42 taper gradually along surfaces 41, 43 as they extend proximally as shown in FIGS. 1 and 2B.

The proximal end 16 of the sleeve body 12 further includes a circular beveled edge 44 which assists insertion of the distal driver portion into the passageway 18. A pair of longitudinally extending outer flat faces 46, 48 align with a package as described in more detail below.

In one construction, the protective carrier 10 has an overall length of 0.45 inch, a diameter of 0.265 inch, and an internal diameter of 0.125 inch. The clearance between the internal ribs 30, 32 is 0.076 inch. The proximal incline surfaces 24 and 41 of flange 22 and slot 40, respectively, is fifteen degrees. The distal face 26 of the flange 22 extends radially inwardly approximately 0.012 inch.

Figure 3A:
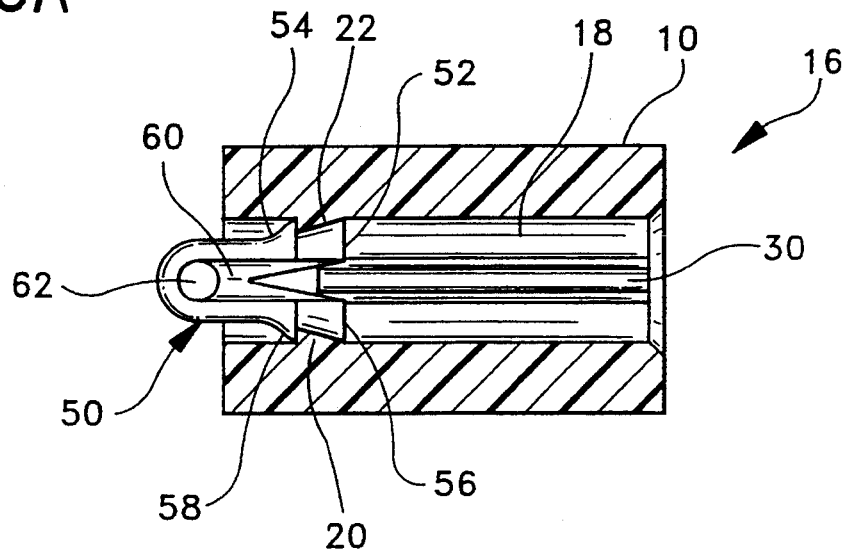
FIG. 3A is a cross-sectional view similar to that of FIG. 2C showing a suture anchor interlocked with the protective carrier.

A suture anchor 50 is shown captured by the protective carrier 10 in FIG. 3A. For this construction, the suture anchor 50 is a Wedge-Style suture anchor having a maximum diameter of 0.118 inch (3.0 mm) and a length of 0.165 inch (4.2 mm). This anchor is inserted into a pre-drilled hole having a diameter of 0.079 inch (2.0 mm) formed in a small bone such as found in the hand or wrist.

In addition to aligning the protective carrier 10 with a driver as described below, the ribs 30, 32 also align the protective carrier 10 with the anchor 50. During assembly, the anchor 50 is inserted through the proximal end 16 after longitudinal suture slots 60 defined by the anchor 50 are aligned with the ribs 30, 32. During insertion past the proximal tapered surfaces 20, 22, the anchor 50 is compressed slightly to enable ridges 54, 58 to slide distally past the flanges 20, 22. Once in the captured position, no stress is placed on the suture anchor 50. The arcuate flange 22 lies in the arcuate groove between arcuate ridges 52, 54 of the anchor 50; similarly, the flange 20 rests between ridges 56, 58 of the anchor 50. Thereafter, the suture anchor 50 can be manipulated by grasping the protective carrier 10 instead of handling the anchor 50; alternatively, the protective carrier 10 can be loaded onto a driver, as described in more detail below, when a user desires to manipulate the anchor 50. In either case, a suture thereafter is threaded through an opening 62 so that a portion of the suture extends to either side of the anchor 50. The suture portions then are pulled proximally to lie within the suture grooves 60 which, by virtue of alignment ribs 30, 32, are aligned with suture slots 40, 42 of the protective carrier 10.

Figure 3B:
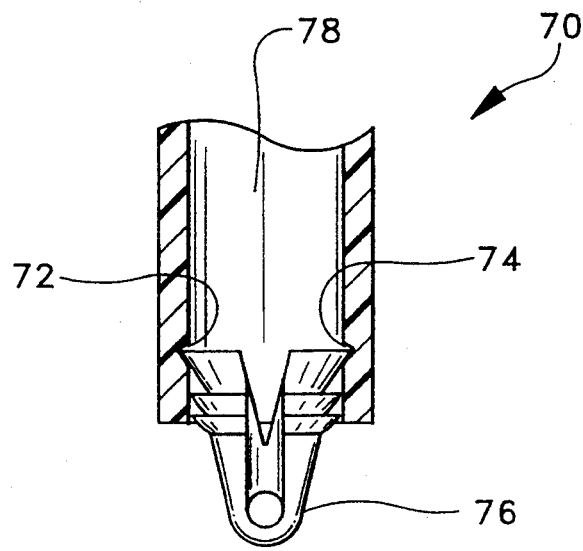
FIG. 3B is a similar cross-sectional view of an alternative protective carrier having an interlocking recess to capture a suture anchor.

An alternative protective carrier 70 is shown in cross-section in FIG. 3B having inner recesses 72, 74 which capture a suture anchor 76. The proximalmost of the three ridges of the suture anchor 76 rest within the recesses 72, 74 to capture the anchor 76 within the protective carrier 70. The suture anchor 76 has a maximum outer diameter of 0.162 inch (4.1 mm), and a length of 0.23 inch (5.8 mm) and is insertable into a drilled hole having a diameter of 0.118 inch (3.0 mm). The inner diameter of passageway 78 is slightly less than 0.162 inch.

Figure 4:
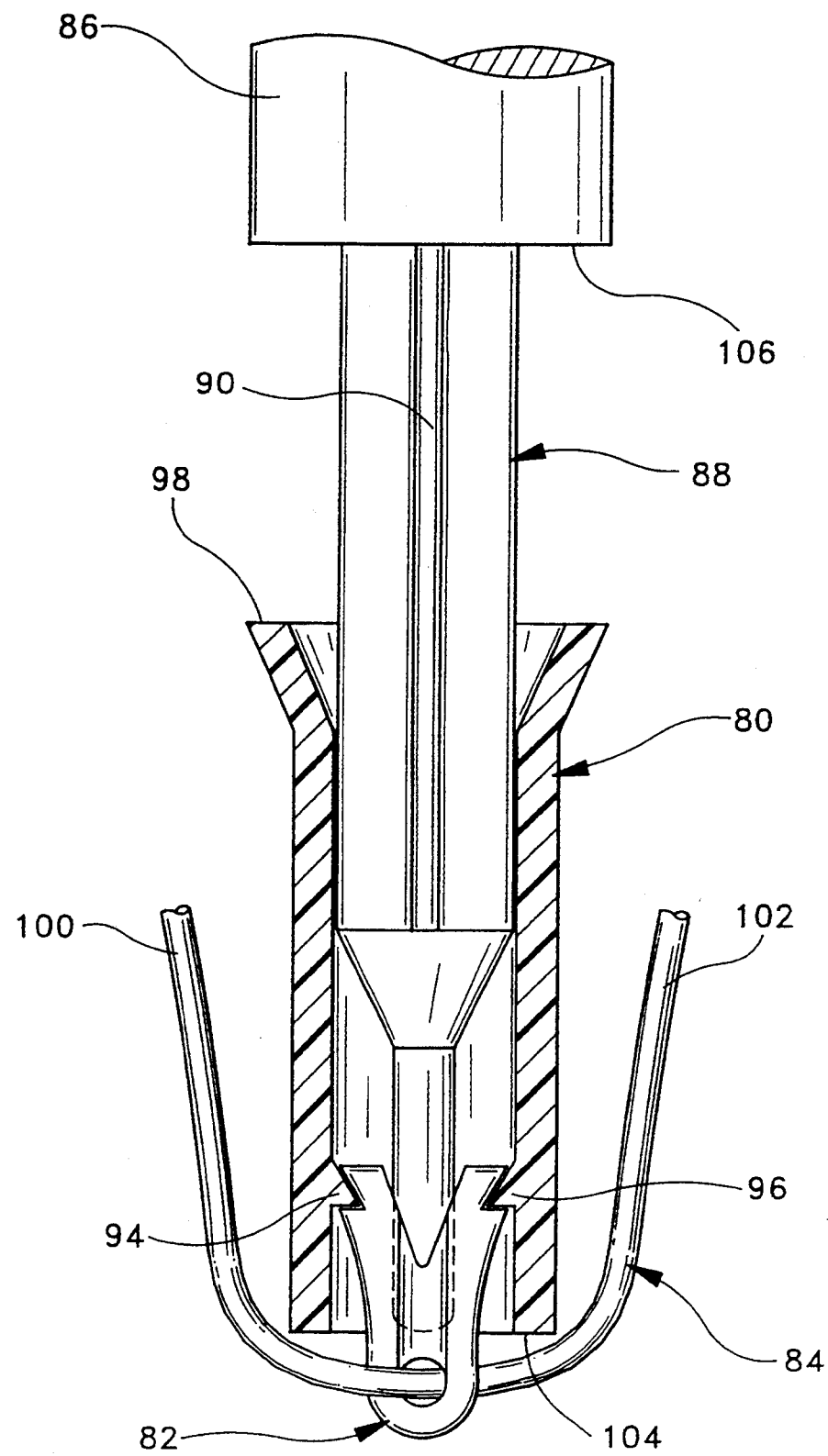
FIG. 4 is a schematic side view of a driver engaged with a suture anchor and an alternative protective carrier according to this invention.

Yet another protective carrier 80, FIG. 4, is shown assembled with a suture anchor 82, a suture 84, and a suture anchor driver 86. The driver 86 has a distal portion 88 with a longitudinal groove 90 alignable with a longitudinal rib (not shown) of the protective carrier 80. The distal portion 88 terminates in a narrow-diameter, blunt drive member 92 which mates with a proximal recess in the suture anchor 82.

The illustrated combination is assembled by sliding the anchor 82 distally through the carrier 80 to lodge projections 94, 96 between the annular ridges of the anchor 82. The distal driver portion 88 then is inserted through the proximal end 98 of the carrier 80 to mate the drive member 92 with anchor 82. A conventional suture threader having a flexible wire tip thereafter is inserted through the opening of the anchor 82 to draw the suture 84 through the opening. The carrier 80 remains associated with the driver 86 by virtue of a slight friction fit between the interior walls of the carrier 80 and the outer surface of the distal driver portion 88; alternatively, the assembly is maintained together by slight pressure exerted on the proximally extending portions 100, 102 of suture 84 which are secured to suture posts on a handle of the driver, such as shown in U.S. Pat. No. 5,100,417, for example.

To install the suture anchor 82 in a patient, an appropriately-sized hole is formed in a bone, and the distal tip of the anchor 82 is placed within the hole. Pressure then is applied to the handle of the driver 86 to force the anchor 82 into the hole. The distal end 104 of the carrier 80 rests against the exterior of the bone. The carrier 80 also serves as a depth stop by limiting insertion when the proximal edge 98 contacts shoulder 106 of the driver 86. Precise placement of the anchor 82 to a desired depth thereby is achieved. The carrier 80 and the driver 86 thereafter are withdrawn, and the carrier 80 discarded in an appropriate manner.

Figure 5A:
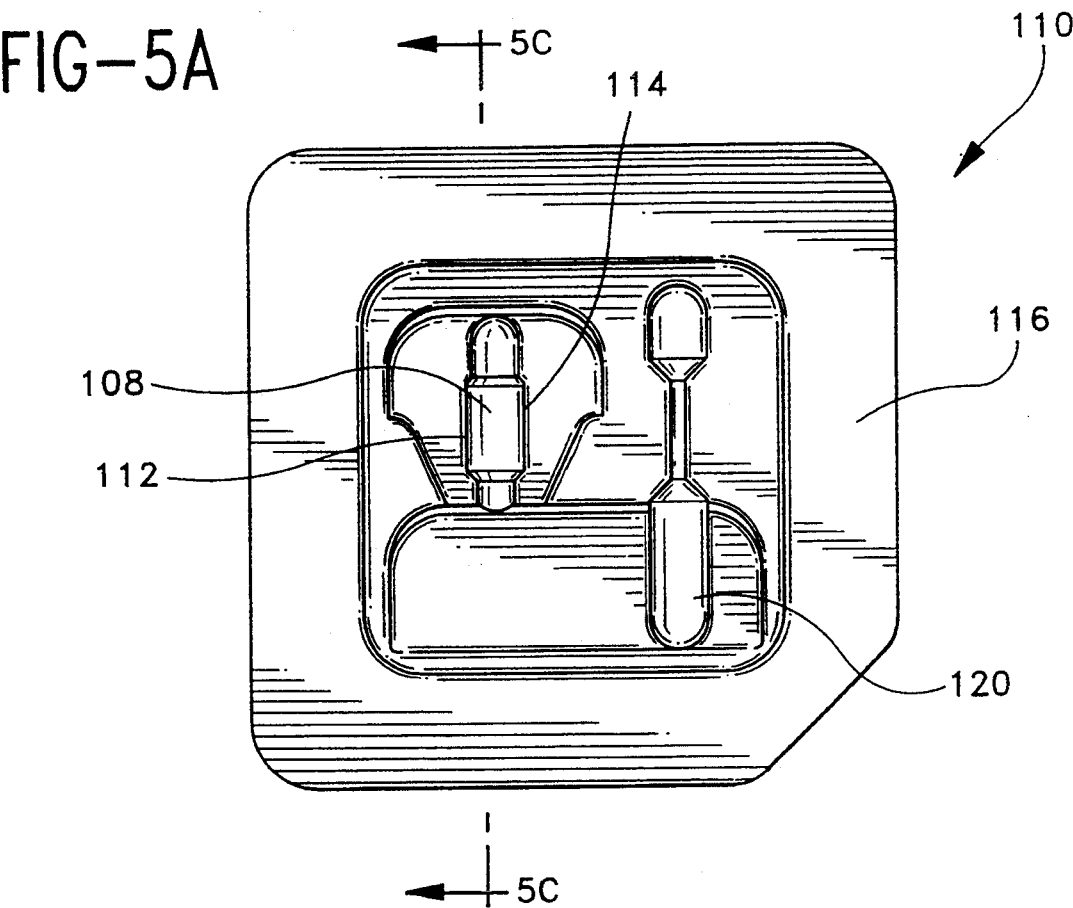
FIG. 5A is a top plan view of a package for carrying a protective carrier according to this invention.
Figure 5B:
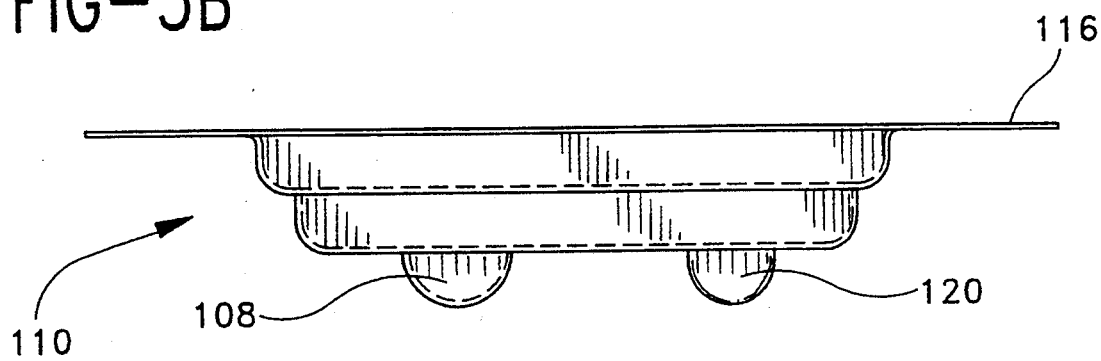
FIG. 5B is an elevational end view of the package of FIG. 5A.
Figure 5C:
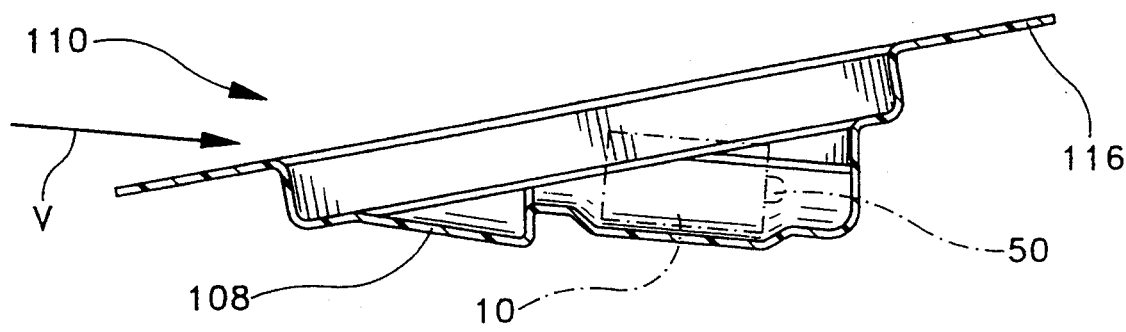
FIG. 5C is a side cut-away view along lines 5C—5C of FIG. 5A.

To achieve maximum benefit from a protective carrier, the suture anchor is installed within a protective carrier at the manufacturing site, placed together in a package, and sterilized. In one construction, the protective carrier and the suture anchor both are formed of a polyacetal polymer such as DELRIN polymer. After the protective carrier 10 and suture anchor 50 are assembled together as shown in FIG. 3A, the assembly is placed within depression 108 of plastic tray 110, FIGS. 5A–5C. Flat faces 46, 48 of the protective carrier 10 are aligned with and held against tray walls 112, 114. The bottom floor of depression 108 is angled relative to the upper surface 116 of the tray 110 to expose the proximal end of the protective carrier 110 as best shown in FIG. 5C.

The tray 110 preferably is formed of a clear, stiff, but slightly resilient material such as polyethylene terephthalate glycol. When the suture anchor is formed of a bioabsorbable material, a paper package may be desirable instead.

After a top covering (not shown) is peeled away by the user, a driver is inserted along vector V. The distal portion of the driver is mated with the carrier 10 and the anchor 50, and the assembly is lifted from the package 110 without having the user touch either the carrier 10 or the anchor 50. An appropriate suture then is threaded through the anchor 50 using a suture threader disposed within depression 120.

A protective carrier according to the present invention therefore isolates a suture anchor or other implant during packaging, sterilization, shipping, storage and during usage. When the length of the protective carrier is coordinated with the distal portion of a driver, the carrier also insures proper insertion depth of the implant. The protective carrier is suitable for use with any implant which can be positively interlocked with the carrier during the above-described stages.

Although specific features of the invention are shown in some drawings and not in others, this is for convenience only as each feature may be combined with any or all of the other features in accordance with the invention.

Other embodiments will occur to those skilled in the art and are within the following claims.

We claim:

1. A combination of a suture anchor, a protective carrier, and a package, the combination comprising:
    a suture anchor;
    a protective carrier including: a sleeve body having a distal end and a proximal end, and defining a passageway extending longitudinally between said distal end and said proximal end; means, disposed in said passageway proximate to said distal end, for interlocking with said suture anchor to capture said suture anchor at least partially within said sleeve body; and means for aligning said sleeve body with a distal portion of a suture anchor driver to inhibit rotation of said sleeve body relative to the driver during and after insertion of the distal driver portion through said passageway;
    a package for carrying said protective carrier with captured suture anchor;
    said protective carrier further including at least one flat face extending longitudinally along a portion of the outer surface of said sleeve body; and
    said package defining a recess having a wall engageable with said flat face to inhibit rotation of said protective carrier relative to said package, said recess in said package being inclined to expose said proximal end of said protective carrier to enable insertion of the distal driver portion into said passageway.

2. The combination of claim 1 wherein said means for interlocking includes at least one flange projecting into said passageway.

3. The combination of claim 2 wherein said means for aligning includes at least one rib projecting into said passageway, said rib being removably insertable into a corresponding groove in the distal driver portion.

4. The combination of claim 3 further including at least one slot in said distal end of said sleeve body for accommodating a portion of a suture carried by the suture anchor.

5. A method of manipulating a suture anchor comprising:
    providing a protective carrier including: a sleeve body having a distal end and a proximal end, and defining a passageway extending longitudinally between the distal end and the proximal end; means, disposed in the passageway proximate to the distal end, for interlocking with the suture anchor to capture the suture anchor at least partially within the sleeve body; and means for aligning the sleeve body with a distal portion of a suture anchor driver to inhibit rotation of the sleeve body relative to the driver during and after insertion of the distal driver portion through said passageway;
    installing the suture anchor within the protective carrier to form an assembly with the suture anchor captured within the carrier;
    placing the assembly within a package for carrying the assembly;
    thereafter inserting a distal portion of the driver through the proximal end of the carrier while the assembly is being carried by the package; and
    removing the assembly from the package using the driver and without otherwise contacting the assembly.

6. The method of claim 5 further including mating the driver with the suture anchor.

7. The method of claim 6 further including threading a suture through an opening in the suture anchor after the suture anchor is mated with the driver and the assembly is removed from the package.

8. The method of claim 7 further including installing the suture anchor within a patient by placing the assembly within the patient and applying force to the driver until the suture anchor separates from the protective carrier and is driven to a desired depth within the patient.

9. A combination of a suture anchor, a suture, a driver and a protective carrier, the combination comprising:
    a suture anchor having means for interacting with a driver at a proximal end of said anchor;
    a suture carried by said suture anchor;
    a suture anchor driver having a distal portion for mating with said means for interacting;
    a protective carrier including: a sleeve body having a distal end and a proximal end, and defining a passageway extending longitudinally between said distal end and said proximal end; means, disposed in said passageway proximate to said distal end, for interlocking with said suture anchor to capture said suture anchor at least partially within said sleeve body; and means for aligning said sleeve body with a distal portion of said suture anchor driver to inhibit rotation of said sleeve body relative to said driver during and after insertion of said distal driver portion through said passageway;

at least one slot in said distal end of said sleeve body for accommodating a portion of said suture therein; and said means for interlocking including at least one flange projecting into said passageway, said means for aligning including at least one longitudinal rib projecting into said passageway, and said distal driver portion defining a longitudinal groove corresponding in shape to said rib, said rib being removably insertable into said corresponding groove.

* * * * *